US012734124B2

(12) United States Patent
Pang et al.

(10) Patent No.: US 12,734,124 B2
(45) Date of Patent: Sep. 15, 2026

(54) EYELASH COATING COMPOSITIONS FOR FALSE EYELASHES

(71) Applicant: L'OREAL, Paris (FR)

(72) Inventors: Christopher Pang, Nanuet, NY (US); Alison Jeanne Scorese, Rahway, NJ (US); Dana M. Cifelli, Clark, NJ (US); Chunhua Li, Hillsborough, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 18/518,099

(22) Filed: Nov. 22, 2023

(65) Prior Publication Data

US 2024/0082142 A1 Mar. 14, 2024

Related U.S. Application Data

(62) Division of application No. 17/462,404, filed on Aug. 31, 2021, now abandoned.

(51) Int. Cl.
*A61K 8/92* (2006.01)
*A61K 8/34* (2006.01)
*A61Q 1/10* (2006.01)

(52) U.S. Cl.
CPC ................ *A61K 8/92* (2013.01); *A61K 8/342* (2013.01); *A61Q 1/10* (2013.01); *A61K 2800/30* (2013.01)

(58) Field of Classification Search
None
See application file for complete search history.

(56) References Cited

U.S. PATENT DOCUMENTS 5,620,693 A * 4/1997 Piot ...................... A61K 8/8158 424/70.7
9,320,920 B2 4/2016 Arditty et al.
9,744,116 B2 * 8/2017 Bolognini ............ A61K 8/8111
2005/0172421 A1 * 8/2005 Jager-Lezer ........... A61K 8/891 8/405
2008/0199415 A1 * 8/2008 Feng ........................ A61Q 1/10 424/70.7
2010/0242984 A1 * 9/2010 Arditty ................ A61K 8/0229 424/70.6
2016/0206031 A1 7/2016 Stoka
2017/0027844 A1 2/2017 Arditty et al.
2018/0104161 A1 4/2018 Siddiqui
2019/0261715 A1 8/2019 Hunter
2020/0281828 A1 * 9/2020 Hunter ................. A61K 8/8147

FOREIGN PATENT DOCUMENTS

FR 3104002 A1 6/2021
WO 2016164001 A1 10/2016
WO 2019/003454 A1 1/2019
WO 2020/172746 A1 9/2020
WO 2021/116601 A1 6/2021

OTHER PUBLICATIONS

Azam "The Ultimate Guide to Fake Lashes, From Someone Who Used to Be Terrified of Them" 2016.*
Label Adhesives & Applications waybackmachine Jul. 17, 2017.*
Combined French Search Report and Written Opinion issued Aug. 22, 2022 in French Patent Application No. 2113900. 13 pages.
Anonymous, "Better Than False Lashes Extreme! Instant Lash Extension Kit", Database GNPD [Online] Mintel; Feb. 20, 2015 (Feb. 20, 2015), XP055950856, Database accession No. 2949807, 7 pages.
Pang, Christopher et al.; International Search Report dated Nov. 17, 2022, for International Patent Application No. PCT/US2022/041965, filed Aug. 30, 2022, 4 pages.
Anonymous, "Database GNPD [Online] Mintel; "Full Volume Fortifying Mascara, Sep. 25, 2001; XP055979753, Database accession No. 10093235 abstract, 2 pages.

* cited by examiner

*Primary Examiner* — Danah Al-Awadi
(74) *Attorney, Agent, or Firm* — Womble Bond Dickinson (US) LLP

(57) ABSTRACT

The invention relates to eyelash coating compositions including water, at least one film-forming agent, at least 8% structuring agent, and at least one surfactant, which can be applied to eyelashes (natural or artificial), and which can be used to attach false (artificial) eyelashes to natural eyelashes, as well as to associated methods.

18 Claims, No Drawings

EYELASH COATING COMPOSITIONS FOR FALSE EYELASHES

CROSS REFERENCE TO RELATED APPLICATION

This application is a divisional of U.S. application Ser. No. 17/462,404, filed Aug. 31, 2021, the entire contents of which are incorporated by reference herein.

FIELD OF THE INVENTION

The present invention relates to eyelash coating compositions comprising water, at least one film-forming agent, at least 8% structuring agent(s), and at least one surfactant. The eyelash coating compositions of the present invention possess sufficient tack and sufficient quick-drying (for example, 1 minute or less) properties such that, after the compositions are applied to eyelashes, false or artificial eyelashes can be adhered to the eyelashes by, through or using the applied eyelash coating compositions of the present invention by placing the false or artificial eyelashes on the applied composition and allowing the eyelash coating composition to dry. Further, the eyelash coating compositions can be applied to false (artificial) eyelashes or natural (real) eyelashes, if desired, to care for or make up the eyelashes and, as such, the eyelash coating compositions of the present invention can be multi-purpose.

DISCUSSION OF THE BACKGROUND

Mascaras typically contain wax which can provide body and volume to the composition. Mascaras can also contain surfactants, particularly when they are in the form of emulsions. However, mascara formulations are typically created to minimize or squelch the full effect of the properties of these ingredients, if present, in an attempt to obtain specific desired properties of the mascara being formulated such as volumization, lengthening, easy removal, etc.

Further, mascara compositions tend to be of two types, (1) water-resistant, long-wearing mascaras which are anhydrous or (2) removable mascaras (for example, removable with soap and water) which contain water. Generally speaking, water-resistant mascaras are not easily removable, and removable mascaras are not particularly long-wearing.

Fake (artificial) eyelashes typically are applied to natural (real) eyelashes through adhesives (glue) or magnets.

For example, US 2016/0206031 discloses the use of magnetic materials, and US 2019/0261715 discloses magnetic materials in an eyeliner-type composition.

With respect to adhesives or glue, US 2017/0027844, WO 2020/172746, and WO 2019/003454 are examples of references disclosing the use of such compounds for false (artificial) eyelashes.

U.S. Pat. No. 9,320,920 discloses compositions for making up eyelashes, including false (artificial) eyelashes.

There remains a need for improved cosmetic compositions having improved cosmetic properties, particularly mascaras and particularly water-containing mascaras, which can be useful for attaching fake (artificial) eyelashes to natural (real) eyelashes, in particular such compositions which do not contain traditional glues or adhesives or magnets such as those used in prior attachment of such false (artificial) products to eyelashes.

Accordingly, one aspect of the present invention is a water-containing care and/or makeup and/or treatment composition for eyelashes which can be used to adhere or bind false (artificial) eyelashes to natural (real) eyelashes.

SUMMARY OF THE INVENTION

The present invention relates to eyelash coating compositions comprising water, at least one film-forming agent, at least 8% structuring agent(s), and at least one surfactant. The eyelash coating compositions of the present invention possess sufficient tack and sufficient quick-drying (for example, 1 minute or less) properties such that, after the compositions are applied to eyelashes, false or artificial eyelashes can be adhered to the eyelashes by, through or using the applied eyelash coating compositions of the present invention by placing the false or artificial eyelashes on the applied composition and allowing the eyelash coating composition to dry. Further, the eyelash coating compositions can be applied to false (artificial) eyelashes or natural (real) eyelashes, if desired, to care for or make up the eyelashes and, as such, the eyelash coating compositions of the present invention can be multi-purpose. Preferably, the composition further comprises at least one coloring agent.

The present invention also relates to eyelash coating compositions comprising water, at least one film-forming agent, at least 8% structuring agent(s), and at least one surfactant, wherein the weight ratio of total amount of structuring agent to total amount of film-forming agent is less than 10:1, preferably less than 8:1, preferably less than 7:1, preferably less than 6:1, preferably less than 4:1, and preferably less than 2:1. Preferably, the weight ratio of total amount of structuring agent to total amount of surfactant is from about 0.4:1 to about 3:1, preferably from about 0.4:1 to about 2.0:1, and preferably from about 0.5:1 to about 1.5:1; and/or the weight ratio of total amount of film-forming agent to total amount of surfactant is from about 0.25:1 to about 3:1, preferably from about 0.33:1 to about 2.0:1, and preferably from about 0.4:1 to about 1.5:1. Preferably, the composition further comprises at least one coloring agent.

The present invention also relates to methods of caring for and/or making up real (natural) eyelashes or false (artificial) eyelashes by applying compositions of the present invention to natural or fake eyelashes in an amount sufficient to care for and/or make up the natural or false eyelashes. Preferably, the composition further comprises at least one coloring agent.

The present invention also relates to methods of applying fake (artificial) eyelashes to real (natural) eyelashes comprising applying compositions of the present invention to natural eyelashes, applying fake eyelashes to the natural eyelashes upon which compositions of the present invention have been previously applied, and allowing the compositions of the present invention to dry so that the fake eyelashes adhere or bind to the natural eyelashes. Preferably, the composition further comprises at least one coloring agent.

It is to be understood that both the foregoing general description and the following detailed description are exemplary and explanatory only, and are not restrictive of the invention.

DETAILED DESCRIPTION OF THE INVENTION

In the following description of the invention and the claims appended hereto, it is to be understood that the terms used have their ordinary and accustomed meanings in the art, unless otherwise specified.

"About" as used herein means within 10% of the indicated number (e.g. "about 10%" means 9%-11% and "about 2%" means 1.8%-2.2%).

"A" or "an" as used herein means "at least one."

"At least one" means one or more and thus includes individual components as well as mixtures/combinations.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Film former", "film-forming polymer" or "film-forming agent" or "co-film former" as used herein means a polymer or resin that leaves a film on the substrate to which it is applied, for example, after a solvent accompanying the film former has evaporated, absorbed into and/or dissipated on the substrate.

"Structuring agent" means any wax or fatty acid or fatty alcohol that is solid at ambient temperature (25° C.), having a melting temperature of more than 30° C. and, for example, more than 45° C., and a hardness of more than 0.5 MPa at ambient temperature.

"Wax" as used herein is a lipophilic fatty compound that is solid at ambient temperature (25° C.) and changes from the solid to the liquid state reversibly, having a melting temperature of more than 30° C. and, for example, more than 45° C., and a hardness of more than 0.5 MPa at ambient temperature.

"Real" and "natural" are used interchangeably throughout this specification.

"False," "fake" and "artificial" are used interchangeably throughout this specification.

"Surfactant" and "emulsifier" are used interchangeably throughout this specification.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C. "Polymer" as used herein means a compound which is made up of at least two monomers.

"Polymer" as used herein means a compound which is made up of at least two monomers.

"Free" or "substantially free" or "devoid of" as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention. Thus, for example, "free of triethanolamine (TEA)" means that an effective amount (that is, more than trace amounts) of TEA is omitted from the composition (that is, about 0% by weight), "substantially free of TEA" means that TEA is are present in amounts not greater than 1% by weight, and "devoid of TEA" means that TEA is present in amounts not greater than 0.5% by weight, based on the total weight of the composition. The same nomenclature applies for all other ingredients identified throughout the application and in this paragraph such as, for example, pressure sensitive adhesive (PSA) ingredients (compositions of the invention which are "free of PSA," "substantially free of PSA," and "devoid of PSA" have meanings consistent with the discussion within this paragraph), even if not specifically discussed for each identified ingredient. The same applies to glues such as, for example, cyanoacrylates ingredients ("free of glue," "substantially free of glue" and "devoid of glue," and "free of cyanoacrylates," "substantially free of cyanoacrylates," and "devoid of cyanoacrylates") and magnets ("free of magnets," "substantially free of magnets," and "devoid of magnets")—such phrases should be understood to have meanings consistent with the discussion within this paragraph. Discussed examples of the use of such language are intended to be exemplary, not limiting.

"Tack" as used herein refers to the quality exhibited by compositions that adhere to an object after application to a substrate. Tack may be evaluated by any method known in the art for evaluating it, such as using a texture analyzer. For example, a sample can be applied to a substrate (for example, a 1 mil drawdown), allowed to dry (for example, for 1 minute), and contacted by an object such as a rubber conical probe (18.3 mm at the tip, 29 mm in height, and 25.4 mm at the base), after which the force associated with removal of the probe from the object can be measured and reported as tack (g). Such measurements can be performed less than 5 minutes after the drying period, such as between 3 and 3½ minutes. Preferably, compositions of the present invention possess tack properties, when determined by this method, of greater than 45 g, preferably greater than 50 g, preferably greater than 70 g, preferably greater than 90 g, and preferably greater than 100 g. So, compositions of the present invention preferably have tack properties ranging from about 30 g to about 200 g, preferably from about 50 g to about 150 g, and preferably from about 70 g to about 130 g, including all ranges and subranges therebetween such as, for example, about 45 g to about 110 g, about 50 g to about 110 g, about 70 g to about 120 g, about 90 g to about 115 g, etc.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to keratin materials such as eyelashes and evaluating the color of the composition after an extended period of time. For example, the color of a composition may be evaluated immediately following application to keratin materials such as eyelashes and these characteristics may then be re-evaluated and compared after a certain amount of time. Further, these characteristics may be evaluated with respect to other compositions, such as commercially available compositions.

"Making up" as used herein means to provide decoration (for example, color) to the eyelashes.

"Protecting" as used herein means to inhibit damage to the eyelashes by providing a protective layer on the eyelashes such as, for example, through application of the compositions of the present invention as a basecoat and/or topcoat composition, and is encompassed within "caring for."

The compositions and methods of the present invention can comprise, consist of, or consist essentially of the essential elements and limitations of the invention described herein, as well as any additional or optional ingredients, components, or limitations described herein or otherwise useful. For example, the surfactant component of the emulsion composition can "consist essentially of" identified surfactant(s) or types of surfactants discussed below.

For purposes of the present invention, the "basic and novel property" associated with compositions, components and methods which "consist essentially of" identified ingredients or actions is "attaching fake eyelashes to natural eyelashes."

Referred to herein are trade names for materials including, but not limited to polymers and optional components. The inventors herein do not intend to be limited by materials described and referenced by a certain trade name. Equivalent materials (e.g., those obtained from a different source under a different name or catalog (reference) number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

All U.S. patents or patent applications disclosed herein are expressly incorporated by reference in their entirety.

Water

According to present invention, compositions comprising water are provided. The compositions of the present invention are not anhydrous. Preferably, compositions of the present invention comprise from about 20% to about 75% water, preferably from about 25% to about 70% water, preferably from about 35% to about 60% water, and preferably from about 40% to about 55% water by weight with respect to the total weight of the composition, including all ranges and subranges therebetween. Preferably, the compositions of the present invention are in the form of an emulsion, with a simple emulsion such as an oil-in-water (O/W) or wax-in-water being the most preferred form.

Film-Forming Agent

According to the present invention, compositions comprising at least one film-forming agent are provided. According to preferred embodiments, the compositions of the present invention comprise at least one dispersion of film forming particles in aqueous phase. The dispersion of film forming particles in aqueous phase is more generally known as latex.

Suitable polymers for the film-forming particles that may be used in the compositions of the present invention include, but are not limited to, synthetic polymers, free-radical type or polycondensate type polymers, polymers of natural origin, and mixtures thereof.

Preferably, the polymers for the film-forming particles may be selected from vinyl (co)polymers, (meth)acrylic (co)polymers, urethanes (co)polymers, and mixtures thereof. Advantageously, the polymer for the film-forming particles is selected from a styrene-(meth)acrylic and (meth) acrylic copolymer, a vinyl acetate and (meth)acrylic copolymer, and mixtures thereof.

Polymers for the film-forming particles of the free-radical type may be chosen, for example, from vinyl polymers or copolymers, such as acrylic polymers.

Vinyl film-forming polymers can result from the polymerization of monomers comprising at least one ethylenic unsaturation and at least one acidic group and/or esters of these acidic monomers and/or amides of these acidic monomers. Monomers comprising at least one acid group which may be used include, for example, α,β-ethylenic unsaturated carboxylic acids such as acrylic acid, methacrylic acid, crotonic acid, maleic acid or itaconic acid. (Meth)acrylic acid and crotonic acid are, for example, used. Preferably, (meth)acrylic acid is used.

The esters of acidic monomers can be chosen, for example, from (meth)acrylic acid esters (also known as (meth)acrylates), such as (meth)acrylates of an alkyl, for example, a C1-C30 alkyl, such as a C1-C20 alkyl, (meth) acrylates of an aryl, such as a C6-C10 aryl, and (meth) acrylates of a hydroxyalkyl, such as a C2-C6 hydroxyalkyl. Among the alkyl (meth)acrylates that may be mentioned, examples include methyl methacrylate, ethyl methacrylate, butyl methacrylate, isobutyl methacrylate, 2-ethylhexyl methacrylate, lauryl methacrylate and cyclohexyl methacrylate. Among the hydroxyalkyl (meth)acrylates that may be mentioned, examples include hydroxyethyl acrylate, 2-hydroxypropyl acrylate, hydroxyethyl methacrylate and 2-hydroxypropyl methacrylate. Among the aryl (meth)acrylates that may be mentioned, examples include benzyl acrylate and phenyl acrylate. The (meth)acrylic acid esters that may be used are, for example, alkyl (meth)acrylates.

The alkyl group of the esters may be substituted. For example, the alkyl group of the esters may be either fluorinated or perfluorinated, i.e., some or all of the hydrogen atoms of the alkyl group are substituted with fluorine atoms. Further, examples of amides of the acid monomers that may be mentioned include (meth)acrylamides, such as N-alkyl (meth)acrylamides, for example, of a $C_2$-$C_{12}$ alkyl. Among the N-alkyl(meth)acrylamides that may be mentioned, examples include N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. For example, these monomers may be polymerized with acid monomers and/or esters thereof and/or amides thereof, such as those mentioned above. Examples of vinyl esters that may be mentioned include vinyl acetate, ethylene vinyl acetate, vinyl neodecanoate, vinyl pivalate, vinyl benzoate and vinyl t-butylbenzoate. Styrene monomers that may be mentioned include styrene and α-methylstyrene.

Among the film-forming polycondensates that may be mentioned, examples include polyurethanes, polyesters, polyesteramides, polyamides, epoxyester resins and polyureas, and modifications or derivatives of any of these.

The polyurethanes may be chosen from anionic, cationic, nonionic or amphoteric polyurethanes, polyurethane-acrylics, polyurethane-polyvinylpyrrolidones, polyester-polyurethanes, polyether-polyurethanes, polyureas and polyurea-polyurethanes, and mixtures thereof.

The polyesters may be obtained, in a known manner, by polycondensation of dicarboxylic acids with polyols, such as diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalene-dicarboxylic acid and 2,6-naphthalenedicarboxylic acid. These dicarboxylic acid monomers may be used alone or as a combination of at least two dicarboxylic acid monomers. Among these monomers, phthalic acid, isophthalic acid and terephthalic acid may, for example, be used.

The diol may be chosen from aliphatic, alicyclic and aromatic diols. The diol used is, for example, chosen from ethylene glycol, diethylene glycol, triethylene glycol, 1,3-propanediol, cyclohexanedimethanol and 4-butanediol. Other polyols that may be used include glycerol, pentaerythritol, sorbitol and trimethylolpropane.

The polyesteramides may be obtained in a manner analogous to that of the polyesters, by polycondensation of diacids with diamines or amino alcohols. Diamines that may be used include, for example, ethylenediamine, hexamethylenediamine and meta- or para-phenylenediamine. An amino alcohol that may be used is, for example, monoethanolamine.

The polyester may also comprise at least one monomer bearing at least one —$SO_3M$ group, wherein M is chosen from a hydrogen atom, an ammonium ion $NH_4^+$ and a metal ion such as an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such an —$SO_3M$ group may, for example, be used.

The aromatic nucleus of the difunctional aromatic monomer also comprising an —$SO_3M$ group as described above may be chosen, for example, from benzene, naphthalene, anthracene, biphenyl, oxybiphenyl, sulfonylbiphenyl and methylenebiphenyl nuclei. Among the difunctional aromatic monomers also comprising an —$SO_3M$ group, mention may be made, for example, of sulfoisophthalic acid, sulfoterephthalic acid, sulfophthalic acid, 4-sulfonaphthalene-2,7-dicarboxylic acid.

The copolymers used are, for example, those based on isophthalate/sulfoisophthalate, such as copolymers obtained by condensation of diethylene glycol, cyclohexanedimethanol, isophthalic acid and sulfoisophthalic acid.

The polymer for the film forming particles may also be a liposoluble polymer. Examples of the liposoluble polymer that may be mentioned include copolymers of a vinyl ester (wherein the vinyl group is directly linked to the oxygen atom of the ester group and the vinyl ester comprises a radical chosen from saturated, linear or branched hydrocarbon-based radicals of 1 to 19 carbon atoms, linked to the carbonyl of the ester group) and of at least one other monomer, which may be a vinyl ester (different from the vinyl ester already present), an α-olefin (comprising from 8 to 28 carbon atoms), an alkyl vinyl ether (the alkyl group of which comprises from 2 to 18 carbon atoms) or an allylic or methallylic ester (comprising a radical chosen from saturated, linear or branched hydrocarbon-based radicals of 1 to 19 carbon atoms, linked to the carbonyl of the ester group).

These copolymers may be crosslinked using crosslinking agents that may be either of the vinylic type or of the allylic or methallylic type, such as tetraallyloxyethane, divinylbenzene, divinyl octanedioate, divinyl dodecanedioate and divinyl octadecanedioate.

Examples of these copolymers which may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Further examples of the liposoluble film-forming polymers include liposoluble copolymers, such as those resulting from the copolymerization of vinyl esters comprising from 9 to 22 carbon atoms or of alkyl acrylates or methacrylates, wherein the alkyl radicals comprise from 10 to 20 carbon atoms. Such liposoluble copolymers may be chosen, for example, from polyvinyl stearate, polyvinyl stearate crosslinked with the aid of divinylbenzene, of diallyl ether or of diallyl phthalate copolymers, polystearyl (meth)acrylate, polyvinyl laurate and polylauryl (meth)acrylate copolymers, it being possible for these poly(meth)acrylates to be crosslinked with the aid of ethylene glycol dimethacrylate or tetraethylene glycol dimethacrylate. The liposoluble copolymers described above are known and are described, for example, in French patent application FR-A-2 232 303; they may have a weight-average molecular weight ranging, for example, from 2,000 to 500,000 such as from 4,000 to 200,000.

Among the liposoluble film-forming polymers which may be used herein, mention may also be made, for example, of polyalkylenes such as copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, homopolymers or copolymers of vinylpyrrolidone (VP), such as copolymers of vinylpyrrolidone and of $C_2$-$C_{40}$ alkene such as $C_3$-$C_{20}$ alkene. In addition to PVP homopolymers, among the VP copolymers which may be used herein, mention may be made, for example, of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

Specific examples of aqueous dispersions of film-forming particles which may be used are the acrylic dispersions sold under the names “Neocryl XK-90®”, “Neocryl A-1070”, “Neocryl A-1090®”, “Neocryl BT-62®”, “Neocryl A-1079®” and “Neocryl A-523®” by the company Avecia-Neoresins, “Dow Latex 432®” by the company Dow Chemical, “Daitosol 5000 AD®” or “Daitosol 5000 SJ” by the company Daito Kasey Kogyo; the aqueous dispersions of polyurethane sold under the names “Neorez R-981®” and “Neorez R-974®” by the company Avecia-Neoresins, “Avalure UR-405®”, “Avalure UR-410®”, “Avalure UR-425®”, “Avalure UR-450®”, “Sancure 875®”, “Sancure 861®”, “Sancure 878®” and “Sancure 2060®” by the company Goodrich, “Impranil 85®” by the company Bayer and “Aquamere H-151®” by the company Hydromer; vinyl dispersions, for instance “Mexomer PAM” and also acrylic dispersions in isododecane, for instance “Mexomer PAP” by the company Chimex.

Further specific examples of latex polymers for use in the present invention further include ethylhexyl acrylate/hema copolymer (and) acrylates/diethylaminoethyl methacrylate/ethylhexyl acrylate copolymer (Syntran®PC 5775), styrene/acrylates/ammonium methacrylate copolymer (Syntran®5760, Syntran®5009, Syntran®PC5620), polyacrylate-21 (and) acrylates/dimethylaminoethyl methacrylate copolymer (Syntran®PC5100, Syntran®PC5776, Eudragit®E 100, Jurymer ET-410C), styrene/acrylates/ammonium methacrylate copolymer (Syntran®5009 CG), olefin/acrylate grafted polymer (and) sodium laureth sulfate (and C12-15 SEC-pareth 15 (Syntran®EX108), acrylates copolymer (Aculyn®33A Polymer, Avalure®Ace 210/120/315 Acrylic Copolymer, Carbopol® Aqua SF-1 Polymer, Coatex®Co 633, Eliclear®380/700/4U, Eudragit® L 100, Joncryl®85, Luviflex®Soft), acrylates/ethylhexyl acrylate copolymer. The Syntran® polymers are commercially available from the supplier Interpolymer Corp.

According to preferred embodiments, compositions of the present invention may comprise instead of, or in addition to, the dispersion of film forming particles in aqueous phase discussed above one or more film-forming agents suitable for use in compositions for application to fake or natural eyelashes. Such film-forming agents can be, for example, water-soluble or liposoluble. Acceptable film-forming are known in the art and include, but are not limited to, those disclosed in U.S. patent application publication no. 2004/0170586, the entire contents of which is hereby incorporated by reference.

Specific examples of film-forming agents include, but are not limited to, proteins, such as proteins of plant origin, such as, for example, wheat or soya proteins; or proteins of animal origin, such as keratins, for example keratin hydrolysates and sulfonic keratins; cellulose polymers, such as, for example, hydroxyethylcellulose, hydroxypropylcellulose, methylcellulose or ethylhydroxyethylcellulose; gums arabic, guar gum, xanthan derivatives or karaya gum; alginates and carrageenans; glycoaminoglycans, hyaluronic acid and its derivatives; shellac resin, other gums such as, for example, gum acacia and gum sandarac, dammars, elemis or copals; muccopolysaccharides, such as chondroitin sulfates, and mixtures thereof.

Specific examples of suitable polymers further include, but are not limited to, polyalkylenes, polyvinylalcohols (PVA), polyvinylpyrrolidone (PVP) or vinylpyrrolidone (VP) homopolymers or copolymers, copolymers of a $C_2$ to $C_{30}$, such as $C_3$ to $C_{22}$ alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer, and mixtures thereof.

Preferred film forming agents include at least one selected from the group of polyvinylpyrrolidone, polyquaternium-11, aluminum starch octenylsuccinate, hydroxyethylcellulose, acacia senegal gum, VP/VA copolymer, poly C10-30 alkyl acrylate, polyvinyl alcohol, styrene/acrylates/ammonium methacrylate copolymer and ethylene/VA copolymer.

Preferably, the film-forming polymers are present in the compositions of the present invention in an amount sufficient to form a film upon the eyelashes. So, for example, when film-forming particles are present in the composition and are in the form of a commercial product containing the film-forming particles in aqueous dispersion, the amount of active material (that is, film-forming particles) within the aqueous dispersion is sufficient to form a film upon the eyelashes.

Preferably, the film-forming polymer(s) is/are present in the compositions of the present invention in amounts of active material (e.g., solid content) generally ranging from about 0.5% to about 40%, preferably from about 1% to about 35%, preferably from about 3% to about 30%, and preferably from about 4% to about 20%, by weight, based on the total weight of the composition, including all ranges and subranges in between, such as, for example 8% to 18%, 2% to 10%, etc.

Surfactant Component

According to the present invention, compositions comprising at least one surfactant are provided. Generally speaking, acceptable surfactants (emulsifiers) can be chose from ionic emulsifiers, nonionic emulsifiers, and mixtures thereof.

"HLB" refers to the "hydrophilic-lipophilic balance" associated with emulsifiers. In particular, "HLB" value relates to the ratio of hydrophilic groups and lipophilic groups in emulsifiers, and also relates to solubility of the emulsifiers. Lower HLB emulsifiers (less than 8 and preferably less than 6) are more soluble in oils (lipophilic material) and are more appropriate for use in water-in-oil (W/O) emulsions. Higher HLB emulsifiers (greater than 8 and preferably greater than 9) are more soluble in water (hydrophilic material) and are more appropriate for oil-in-water (O/W) emulsions.

By way of example, the following emulsifiers have been reported to have the following HLB values:

Propylene Glycol Isostearate HLB=2.5;
Glyceryl Stearate HLB=3.8;
Sorbitan Isostearate HLB=4.7;
Oleth-2 HLB=4.9;
Glyceryl Laurate HLB=5.2;
Ceteth-2 HLB=5.3;
Methyl Glucose Sesquistearate HLB=6.6;
Ceteth-30 HLB=16.5;
$C_{12}$-13 pareth-23 HLB=16.7;
Polysorbate 20 HLB=16.7;
Laureth-23 HLB=16.9;
PEG-100 Stearate HLB=18.8; and
Sodium lauryl sulfate HLB=40.

According to preferred embodiments, compositions of the present invention comprise at least one surfactant which has an HLB value which is greater than 8, and at least one surfactant which has an HLB value of less than 8.

According to preferred embodiments, one or more of the emulsifiers is a fatty alcohol, a fatty acid, or ester thereof, optionally alkoxylated (ethoxylated, propoxylated, etc.), glycerylated and/or pegylated. Fatty acids correspond the formula R—COOH and fatty alcohols correspond to the formula R—OH, in which R denotes a saturated or unsaturated hydrocarbon radical preferably having from 7 to 45 carbon atoms, preferably from 9 to 35 carbon atoms, preferably from 15 to 35 carbon atoms, preferably from 15 to 21 carbon atoms, and preferably from 16 to 18 carbon atoms. Mention may be made of, for example, lauric acid/alcohol, stearic acid/alcohol, oleic acid/alcohol, behenyl acid/alcohol, cetyl acid/alcohol and mixtures thereof (including cetearyl compounds).

Suitable emulsifiers include ethoxylated fatty acids or alcohols, ethoxylated fatty acids, partial glycerides of ethoxylated fatty acids or alcohols, glycerolated fatty acids or alcohols, and mixtures thereof.

Suitable alkoxylated fatty alcohols include, for example, the addition products of ethylene oxide with lauryl alcohol, in particular those containing from 2 to 250 oxyethylenated groups (having CTFA names Laureth-2 to Laureth-250); the addition products of ethylene oxide with behenyl alcohol, in particular those containing from 2 to 250 oxyethylenated groups (having CTFA names Beheneth-2 to Beheneth-250); the addition products of ethylene oxide with cetearyl alcohol (mixture of cetyl alcohol and of stearyl alcohol) in particular those containing from 2 to 250 oxyethylenated groups (having CTFA names Ceteareth-2 to Ceteareth-250 such as, for example, Ceteareth-33); the addition products of ethylene oxide with cetyl alcohol, in particular those containing from 2 to 250 oxyethylenated groups (having CTFA names Ceteth-2 to Ceteth-250 such as, for example, Ceteth-30); the addition products of ethylene oxide with stearyl alcohol, in particular those containing from 2 to 250 oxyethylenated groups (having CTFA names Steareth-2 to Steareth-250 such as, for example, and Steareth-20); the addition products of ethylene oxide with isostearyl alcohol, in particular those containing from 2 to 250 oxyethylenated groups (having CTFA names Isosteareth-2 to Isosteareth-250); and mixtures thereof, wherein the amount of alkoxylation preferably ranges from 2 to 250, and preferably from 5 to 200, including all ranges and subranges therebetween including, for example, 10 to 100, 50 to 150, etc.

Suitable alkoxylated fatty acid include, for example, the addition products of ethylene oxide with lauric acid, palmitic acid, stearic acid or behenic acid, and mixtures thereof, in particular those containing from 2 to 250 oxyethylenated groups, such as, for example, laurates of PEG-2 to PEG-50 (having CTFA names: PEG-2 laurate to PEG-50 laurate); palmitates of PEG-2 to PEG-50 (having CTFA names: PEG-2 palmitate to PEG-50 palmitate); stearates of PEG-2 to PEG-250 (having CTFA names: PEG-2 stearate to PEG-250 stearate such as PEG-100 stearate and PEG-200 stearate); palmitostearates of PEG-2 to PEG-50; behenates of PEG-2 to PEG-50 (having CTFA names: PEG-2 behenate to PEG-50 behenate); and mixtures thereof, wherein the amount of alkoxylation preferably ranges from 2 to 250, and preferably from 5 to 200, including all ranges and subranges therebetween including, for example, 10 to 100, 50 to 150, etc.

Suitable glycerylated fatty acids include, for example, glyceryl stearate, glyceryl oleate and glyceryl caprylate.

According to preferred embodiments, the surfactant component may additionally contain or comprise at least one alkyl phosphate surfactant as disclosed, for example, in U.S. Pat. No. 9,687,426, the entire contents of which is hereby incorporated by reference. Preferably, if present, the alkyl phosphate surfactant is chosen from C14-C24, preferably C16-C18 alkyl phosphates, and mixtures thereof. Even more preferably, they are chosen from cetyl phosphate, stearyl phosphate and cetearyl phosphate. For example, cetyl phosphate is commercially available under the names Amphisol K (Roche), Amphisol A (Roche), Arlatone MAP (Uniqema) and Crodafos MCA (Croda). It is to be understood that "alkyl phosphate" includes salts of such compounds such as potassium cetyl phosphate.

Preferred surfactants include at least one selected from the group of palmitic acid, potassium cetyl phosphate, ceteareth-33, steareth-2, steareth-20, glyceryl stearate and stearic acid.

Preferably, the surfactant(s) (surfactant component) is/are present in the compositions of the present invention in an amount of from about 4% to about 20%, preferably from about 5% to about 17.5%, preferably from about 5% to about 15%, and preferably from about 6% to about 12%, by weight based on the total weight of the composition, including all ranges and subranges in between.

Structuring Agents

According to the present invention, compositions comprising at least 8% structuring agent(s) are provided. "Structuring agent" is defined above.

Suitable fatty acids or alcohols include compounds containing 8 or more carbon atoms which are solid at or above ambient temperature such as, for example, solid at 30° C., preferably solid at 35° C., preferably solid at 40° C., and preferably solid at 45° C. Examples of such compounds include stearic acid, cetyl alcohol, stearyl alcohol, cetearyl alcohol, etc.

Suitable waxes can be hydrocarbon, fluorinated and/or silicone, and be of plant, mineral, animal and/or synthetic origin.

Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice or rice bran wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C., silicone waxes, such as alkyl- or alkoxydimethicones having an alkyl or alkoxy chain ranging from 10 to 45 carbon atoms, poly(di)methylsiloxane esters which are solid at 30° C., and whose ester chain comprising at least 10 carbon atoms, or else di(1,1,1-trimethylolpropane) tetrastearate, which is sold or manufactured by Heterene under the name HEST 2T-4S, and mixtures thereof.

Further suitable examples of wax include, but are not limited to, BIS-PEG-12 DIMETHICONE CANDELILLATE wax such as for example the Siliconyl Candelilla Wax marketed by the company KOSTER KEUNEN, hydrogenated Jojoba wax such as for example that marketed by the company DESERT WHALE, hydrogenated palm oil such as that marketed by the company SIO, rice bran wax, Sumac wax, ceresin waxes, laurel wax, Chinese insect wax, Shellac wax, hydrogenated olive oil such as Waxolive from the company SOLIANCE, waxes obtained by hydrogenation of olive oil esterified with C12 to C18 chain fatty alcohols such as those sold by the company SOPHIM under the brand names Phytowax Olive 12L44, 14L48, 16L55 and 18L57, waxes obtained by hydrogenation of castor oil esterified with cetyl or behenyl alcohol such as for example those which are sold under the names Phytowax Ricin 16 L 64 and Phytowax Ricin 22 L 73 by the company SOPHIM, hydrogenated Cameline wax, Ouricury wax, Montan wax, ozokerite waxes such as for example Wax SP 1020 P marketed by the company Strahl & Pitsch, microcrystalline waxes such as for example that sold under the brand name Microwax HW by the company PARAMELT, triglycerides of lauric, palmitic, cetylic and stearic acids (INCI name: hydrogenated coco glycerides) such as for example that sold under the brand name Softisan 100 by the company SASOL, polymethylene waxes such as for example that sold under the brand name Cirebelle 303 by the company SASOL, polyethylene waxes such as for example those sold under the brand names Performalene 400 polyethylene, Performalene 655 polyethylene and Performalene 500-L polyethylene by the company New Phase Technologies, alcohol-polyethylene waxes such as for example that marketed under the name Performacol 425 Alcohol by the company BARECO, the 95/5 ethylene/acrylic acid copolymer sold under the brand name AC 540 wax by the company Honeywell, hydroxyoctacosanyl hydroxy-stearate such as for example that sold under the brand name Elfacos C 26 by the company AKZO, octacosanyl stearate such as for example that marketed under the name Kester Wax K 82H by the company KOSTER KEUNEN, stearyl stearate such as for example that marketed under the name Liponate SS by the company LIPO CHEMICALS, pentaerythritol distearate such as for example that marketed under the name Cutina PES by the company COGNIS, the mixture of dibehenyl adipate, dioctadecyl adipate and di-eicosanyl adipate (INCI name C18-C22 dialkyl adipate), the mixture of dilauryl adipate and ditetradecyl adipate (INCI name: C12-C14 dialkyl adipate), the mixture of dioctadecyl sebacate, didocosyl sebacate and dieicosyl sebacate (INCI name: C18-C22 dialkyl sebacate) and the mixture of dioctadecyl octadecanedioate, didocosyl octanedioate and dieicosyl octanedioate (INCI name: C18-C22 dialkyl octanedioate) such as for example those marketed by the company COGNIS, pentaerythrityl tetrastearate such as for example Liponate PS-4 from the company Lipo Chemicals, tetracontanyl stearate such as for example Kester Wax K76H from the company KOSTER KEUNEN, stearyl benzoate such as for example Finsolv 116 from the company FINETEX, behenyl fumarate such as for example Marrix 222 from the company AKZO BERNEL, di-(trimethylol-1,1,1-propane) tetrastearate such as for example that which is offered under the name "HEST 2T-4S" by the company HETERENE, didotriacontanyl distearate such as for example Kester Wax K82D from the company KOSTER KEUNEN, polyethylene glycol montanate with 4 ethylene oxide units (PEG-4) such as for example that which is sold under the brand name Clariant Licowax KST1, hexanediol disalicylate such as for example Betawax RX-13750 marketed by the company CP Hall, dipentaerythritol hexastearate such as for example that which is sold under the brand name Hest 2P-6S by the company HETERENE, ditrimethylolpropane tetrabehenate such as for example that which is sold under the brand name Hest 2T-4B by the company HETERENE, Jojoba esters such as for example that which is sold under the brand name Floraester HIP by the company FLORATECH, mixtures of linear (C20-40) carboxylic acid/saturated hydrocarbons (INCI name: C20-40 acid polyethylene) such as for example Performacid 350 acid from the company NEW PHASE TECHNOLOGIES, synthetic wax of the Fischer-Tropsch type such as that marketed under the name Rosswax 100 by the company ROSS, cetyl alcohol, stearyl alcohol, behenyl alcohol, dioctadecyl carbonate such as for example Cutina KE 3737, saccharose polybehenate such as for example Crodaderm B from the company CRODA, waxes of plant origin such as carnauba wax, candelilla wax, hydrogenated jojoba wax, sumac wax, waxes obtained by hydrogenation of olive oil esterified with C12 to C18 chain fatty alcohols sold by the company SOPHIM in the Phytowax range (12L44, 14L48, 16L55 and 18L57), rice bran wax, cetyl, laurel wax, Ouricury wax and mixtures thereof can be mentioned.

Preferred structuring agents include at least one selected from the group of cetearyl alcohol, carnauba wax, glyceryl behenate, glyceryl dibehenate, tribehenin, bis-diglyceryl polyacyladipate-2, paraffin, cetyl alcohol, hydrogenated jojoba oil, hydrogenated palm oil, *Oryza sativa* (rice) bran wax, jojoba butter and candilla wax.

Preferably, the structuring agent(s) are present in the compositions of the present invention in a total amount ranging from 8% to about 45% by weight, preferably from about 10% to about 40% by weight, and preferably from about 15% to about 35% by weight, based on the total weight of the composition, including all ranges and subranges within these ranges such as, for example, 8% to 17%, 10% to 25%, 20% to 30%, etc.

Preferably, structuring agent(s) and surfactant(s) are present in the compositions of the present invention in weight ratios of structuring agent to surfactant of from about 0.4:1 to about 3:1, preferably from about 0.4:1 to about 2.0:1, and preferably from about 0.5:1 to about 1.5:1.

Preferably, structuring agent(s) and film-forming agent(s) are present in the compositions of the present invention in weight ratios of less than 10:1, preferably less than 8:1, preferably less than 7:1, preferably less than 6:1, preferably less than 4:1, and preferably less than 2:1.

Preferably, film forming agent(s) and surfactant(s) are present in the compositions of the present invention in weight ratios of from about 0.25:1 to about 3:1, preferably from about 0.33:1 to about 2.0:1, and preferably from about 0.4:1 to about 1.5:1.

When calculating the above ratios, it should be understood that if a particular ingredient is counted as a structuring agent, it may not also be counted as one of the other identified categories of ingredients. For example, solid fatty compounds such as stearic acid, cetyl alcohol, cetearyl alcohol, etc. are included in total amount of structuring agent present but may not also be included in total amount of surfactant present. Calculated ratios herein have been calculated in this manner.

Oil Phase

According to embodiments of the present invention, the compositions of the present invention may optionally further comprise at least one oil. "Oil" means any non-aqueous medium which is liquid at ambient temperature (25° C.) and atmospheric pressure (760 mm Hg). Suitable oils can be volatile or non-volatile.

Suitable oils include volatile silicone oils. Examples of such volatile silicone oils include linear or cyclic silicone oils having a viscosity at room temperature less than or equal to 6cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Suitable oils include non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Suitable oils include synthetic oils or esters of formula $R_5OOOR_6$ in which $R_5$ represents a linear or branched higher fatty acid residue containing from 1 to 40 carbon atoms, including from 7 to 19 carbon atoms, and R6 represents a branched hydrocarbon-based chain containing from 1 to 40 carbon atoms, including from 3 to 20 carbon atoms, with $R_6$+R7≥10, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; pentaerythritol esters; and synthetic ethers containing from 10 to 40 carbon atoms.

If present, the oil(s) is/are present in the compositions of the present invention in an amount ranging from about 0.1% to about 20% by weight, more preferably from about 0.4% to about 15% by weight, and preferably from about 0.5% to about 10% by weight, based on the total weight of the composition, including all ranges and subranges within these ranges.

According to preferred embodiments, however, compositions of the present invention are substantially free of, devoid of, or free of volatile oils such as, for example, isododecane.

According to preferred embodiments, compositions of the present invention are substantially free of, devoid of, or free of silicone oils such as, for example, dimethicone.

According to preferred embodiments, the oil component of the compositions of the present invention consist of non-volatile oils.

According to preferred embodiments, the oil component of the compositions of the present invention consist of hydrocarbon oils.

According to preferred embodiments, the oil component of the compositions of the present invention consist of non-volatile hydrocarbon oils.

Coloring Agents

According to preferred embodiments of the present invention, compositions optionally further comprising at least one coloring agent are provided. Preferably, such colored compositions can be cosmetic compositions such as mascaras.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 25% by weight of the total weight of the composition, such as from 2.5% to 20%, and further such as from 5% to 15%, including all ranges and subranges therebetween.

However, it is possible for the compositions of the present invention to be free, substantially free, or devoid of coloring agents as defined above.

Additional Additives

The composition of the invention can also comprise any additive usually used in the field under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, silicone elastomers, pasty compounds, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* (9th ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

According to preferred embodiments of the present invention, methods of caring for and/or making up eyelashes (artificial or natural) by applying compositions of the present invention to the eyelashes in an amount sufficient to care for and/or make up the eyelashes are provided. Preferably, "making up" the keratin material includes applying at least one coloring agent to the eyelashes in an amount sufficient to provide color to the eyelashes.

In accordance with the preceding preferred embodiments, the compositions of the present invention are applied topically to the desired area of the eyelashes in an amount sufficient to care for and/or make up the eyelashes. The compositions may be applied to the desired area as needed, preferably once or twice daily, more preferably once daily and then preferably allowed to dry before subjecting to contact such as with clothing or other objects (for example, a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

According to preferred embodiments of the present invention, methods of applying fake (artificial) eyelashes to real (natural) eyelashes comprising applying compositions of the present invention to natural eyelashes, applying fake eyelashes to the natural eyelashes upon which compositions of the present invention have been previously applied, and allowing the compositions of the present invention to dry so that the fake eyelashes attach to the natural eyelashes are provided. Preferably, the composition further comprises at least one coloring agent.

In accordance with the preceding preferred embodiments, the compositions of the present invention are applied topically to the desired area of the eyelashes in an amount sufficient to attach false (artificial) eyelashes to natural eyelashes. The compositions may be applied to the desired area as needed, preferably once or twice prior to attachment of the artificial eyelashes, and then allowed to dry after contacting the applied composition with artificial eyelashes for attachment to eyelashes. Preferably, the artificial eyelashes are contacted with the applied composition less than 1 minute after the composition has been applied to natural eyelashes, more preferably less than 45 seconds after application.

Typically, artificial eyelashes attached to natural eyelashes do not need special removal techniques, and can be removed by gently pulling them away from eyelashes. However, typical removal methods and solutions can be used to remove the artificial eyelashes from natural eyelashes, if desired.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example I—Sample Formulations

| Ingredient | Preferred Range | Specific Range |
|---|---|---|
| Wax/structuring agent | 8-45% | 8-17% |
| Film Former | 4-20% | 8-18% |
| Emulsifier | 4-20% | 6-12% |
| Pigment | 2.5-20% | 5-15% |
| Solvent | 20-75% | 35-60% |
| Other (preservative, fiber, etc.) | 0-5% | 0-2% |

Example II—Composition Preparation

The compositions can be prepared in a customary manner for mascara products. Compositions in Example I can be prepared by combining all oil phase ingredients including structuring agents in a side kettle, and then combining the oil phase ingredients with the main water phase including water-soluble material in the main kettle to prepare the composition.

Example III—Testing Protocols

Compositions falling within the "preferred ranges" for ingredients in example I were prepared. These compositions had the following weight ratios:

| Composition | Wax to Surfactant | Wax to Film Former | Film Former to Surfactant | Tack (g) (Std. Dev.) |
|---|---|---|---|---|
| Comp. 1 (t) | 2.1 | 10.8 | 0.2 | 35 (10.3) |
| Inv. 1 (sm) | 1.5 | 0.9 | 1.5 | 108 (24.1) |
| Inv. 2 (cdo) | 0.6. | 0.60 | 1.0 | 92 (33.6) |
| Inv. 3 (fll) | 0.99 | 1.2 | 0.8 | 70 (10.3) |
| Inv. 4 (sh) | 2.75 | 6 | 0.45 | 57 (17.2) |

Tack was determined via the protocol described above, run in triplicate. In particular, a sample was prepared by using a 1 mil drawn down bar to create a 1 mil thick film on a stainless steel substrate. After drying for 3 min, the tack was measured by using a rubber probe on TA XTPlus Texture Analyzer. A force of 2 gram was applied to the film using the rubber probe. As the rubber probe retracted from the film, the amount of force was measured for determining tack.

As can be seen from the above testing, all compositions having a weight ratio of total amount of structuring agent to total amount of film-forming agent of less than 10:1 possessed tack of >45 g, in particular >57 g, whereas the comparative composition with a weight ratio slightly higher than 10 did not. This testing demonstrated the result effective nature of the structuring agent to film-forming agent weight ratio in the tested compositions.

Similarly, all compositions having a weight ratio of total amount of film-forming agent to total amount of surfactant of greater than 0.25:1 possessed tack of >45 g, in particular >57 g, whereas the comparative composition with a weight ratio slightly lower than 0.25:1 did not. This testing demonstrated the result effective nature of the film-forming agent to surfactant weight ratio in the tested compositions.

What is claimed is:

1. A method of applying artificial eyelashes to natural eyelashes consisting of applying an eyelash coating composition comprising water, at least one film-forming agent, at least 8% structuring agent, and at least one surfactant, wherein the weight ratio of total amount of structuring agent to total amount of film-forming agent is less than 10:1 and wherein the weight ratio of total amount of film-forming agent to total amount of surfactant in the composition is from about 0.25:1 to about 3:1, to natural eyelashes, applying artificial eyelashes to the natural eyelashes upon which the composition has been applied, and allowing the composition to dry so that the artificial eyelashes attach to the natural eyelashes.

2. The method of claim 1, wherein the weight ratio of total amount of structuring agent to total amount of surfactant in the composition is from about 0.4:1 to about 3:1.

3. The method of claim 1, wherein the composition is a mascara.

4. The method of claim 1, wherein the composition further comprises at least one coloring agent.

5. The method of claim 1, wherein the composition is in the form of an oil-in-water emulsion or a wax-in-water emulsion.

6. The method of claim 1, wherein the composition comprises:

35% to 60% water,

15% to 35% total amount of film forming agent,

15% to 40% total amount of structuring agent, and

5% to 20% total amount of surfactant, all percentages being based on weight with respect to the total weight of the composition.

7. The method of claim 1, wherein the at least one surfactant in the composition is selected from the group consisting of fatty alcohols and fatty acids, optionally alkoxylated, glycerylated and/or pegylated.

8. The method of claim 1, wherein the at least one surfactant in the composition is selected from the group consisting of steareth-2 to steareth-20.

9. The method of claim 1, wherein the composition is free of volatile oils.

10. The method of claim 1, wherein the composition is free of cyanoacrylates.

11. The method of claim 1, wherein the composition has tack properties of at least 45 g.

12. The method of claim 1, wherein the weight ratio of total amount of structuring agent to total amount of film-forming agent is less than 7:1.

13. The method of claim 1, wherein the weight ratio of total amount of structuring agent to total amount of film-forming agent is less than 2:1.

14. The method of claim 1, wherein the weight ratio of total amount of film-forming agent to total amount of surfactant in the composition is from about 0.33:1 to about 2:1.

15. The method of claim 1, wherein the weight ratio of total amount of film-forming agent to total amount of surfactant in the composition is from about 0.4:1 to about 1.5:1.

16. The method of claim 13, wherein the weight ratio of total amount of film-forming agent to total amount of surfactant in the composition is from about 0.4:1 to about 1.5:1.

17. The method of claim 1, wherein the composition has tack properties of at least 70 g.

18. The method of claim 16, wherein the composition has tack properties of at least 70 g.

* * * * *